| United States Patent [19] | [11] | 4,131,608 |
|---|---|---|
| Zirngibl et al. | [45] | Dec. 26, 1978 |

[54] THIOETHERS

[75] Inventors: Ludwig Zirngibl, Zofingen; Johanna Fischer, Reiden; Kurt Thiele, Zofingen, all of Switzerland

[73] Assignee: Siegfried Aktiengesellschaft, Zofingen, Switzerland

[21] Appl. No.: 795,224

[22] Filed: May 9, 1977

[30] Foreign Application Priority Data

May 12, 1976 [CH] Switzerland .................. 5930/76

[51] Int. Cl.$^2$ .................................. C07D 263/58
[52] U.S. Cl. ........................ 260/307 D; 548/336; 544/316; 546/278; 546/157; 260/302 H; 260/306.6 R; 260/306.7 R; 424/251; 424/258; 424/263; 424/269; 424/270; 424/272; 424/273 R
[58] Field of Search .................. 260/307 D; 424/272

[56] References Cited

U.S. PATENT DOCUMENTS

| 2,820,042 | 1/1958 | Katz et al. ........................ 260/307 |
|---|---|---|
| 3,984,426 | 10/1976 | Winkelmann et al. .......... 260/302 H |

OTHER PUBLICATIONS

R. Morrison & R. Boyd, "Organic Chemistry", Allyn and Bacon, Inc., Boston, 1974–(3rd Edition) p. 457.

*Primary Examiner*—Paul M. Coughlan, Jr.
*Assistant Examiner*—Lisa Jones
*Attorney, Agent, or Firm*—Werner W. Kleeman

[57] ABSTRACT

This invention relates to novel thioethers as well as to the addition salts thereof with inorganic or organic acids. The novel compounds and their addition salts have valuable anti-mycotic and fungicidal properties. Further the invention relates to a process for preparing the novel compounds and their addition salts, and to anti-mycotic and fungicidal compositions containing the novel thioethers, or addition salts thereof, as the active constituent.

1 Claim, No Drawings

THIOETHERS

BACKGROUND OF THE INVENTION

1. Field of the Invention

The present invention relates to novel organic compounds of the thioether class and to the addition salts of such compounds with inorganic or organic acids. The invention further relates to a process for producing the novel thioethers and their addition salts, as well as to anti-mycotic pharmaceutical compositions and to fungicidal agrochemical compositions containing the novel thioethers or their addition salts as an active component.

2. Description of the Prior Art

Various classes of organic compounds are known to be effective against mycobacteria and fungi. However, as a broad spectrum of effective anti-mycotic and fungicidal agents is desirable both in view of improved effectiveness against known mycobacteria and fungi, and against mutations or hitherto unknown species, continued efforts are made to find new agents for replacing or complementing the existing means for treating mycotic diseases and for controlling fungus growth.

Certain organic sulphur compounds of the thioether class are known to exhibit anti-mycotic activity, cf. for example the compounds disclosed in Belgian Patent No. 841,309 and German Published Specification DT-OS 2 541 833. In view of the above general aims of the art, novel and effective agents for treating mycoses and fungus infections remain an important research target.

Thus, it is a general object of the invention to provide for novel compounds having an anti-mycotic or fungicidal effectiveness.

A further object of the invention is a process for producing novel compounds.

Another object of the invention is an anti-mycotic composition for pharmaceutical use.

Yet another object of the invention is a fungicidal composition for agricultural use.

SUMMARY OF THE INVENTION

According to a first embodiment, the invention provides for novel compounds of the formula (I)

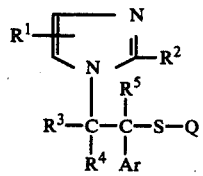

and for addition salts of the formula (I) compound with organic or inorganic acids.

In the above formula (I)

$R^1$ is hydrogen, lower alkyl, halogen or nitro, $R^2$ is hydrogen, lower alkyl, halogen, nitro or hydroxy-substituted lower alkyl, $R^3$ is hydrogen, lower alkyl, hydroxy-substituted lower alkyl, lower alkyloxy, lower alkylthio, $C_6$-$C_{10}$ aryloxy or $C_6$-$C_{10}$ arylthio, $R^4$ is hydrogen or lower alkyl, and $R^5$ is hydrogen, lower alkyl, lower alkoxy, lower alkylthio, $C_6$-$C_{10}$ aryloxy or $C_6$-$C_{10}$ arylthio.

If two mutually adjacent groups $R^3$, $R^4$ and $R^5$ in formula (I) are lower alkyl, such two groups may together form an alicyclic ring including from 3 to 8 C-atoms.

Ar in formula (I) is a mononuclear or binuclear carbocyclic or heterocyclic ring structure in which at least one nucleus is aromatic, and Q is a heterocyclic ring structure.

The term "lower alkyl" as used in all of the above definitions includes straight or branched chain alkyls consisting of from 1 to 6 C-atoms, preferably of from 1 to 4 C-atoms. Methyl and ethyl are particularly preferred. The term "halogen" includes chlorine, bromine and iodine atoms. Chlorine is the generally preferred halogen.

The ring structures represented by Ar and Q in formula (I) may be unsubstituted or carry one or more like or different substituents selected, for example, from halogen, lower alkyl, alkoxy, alkylmercapto, cycloalkyl, aryl, aralkyl and nitro.

According to a second embodiment, the invention provides a process for preparing the formula (I) compounds and their addition salts by condensing a compound of the formula (II)

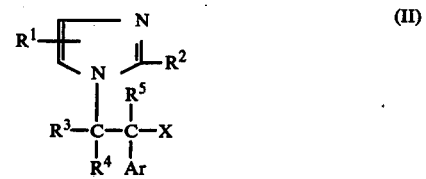

with a compound of formula (III)

Y - Q (III)

wherein $R^1$, $R^2$, $R^3$, $R^4$, $R^5$, Ar and Q have the significance given above for formula (I), while X and Y represent radicals capable of being split-off under the condensation conditions of employed (leaving) groups but providing the sulphur atom of the target compound. In other words, one of the leaving groups comprises a sulphur atom that remains in the condensation product and is not removed with the leaving groups.

According to a third embodiment, the invention provides for an anti-mycotic composition suitable for pharmaceutical use and comprising (a) at least one compound of formula (I) and/or an addition salt thereof with a pharmaceutically acceptable acid in admixture with (b) a pharmaceutically acceptable carrier or vehicle that may be a solid or a liquid including highly viscous liquids or pastes.

According to a fourth embodiment, the invention provides for a fungicidal composition comprising (a) at least one formula (I) compound and/or an addition salt thereof with an organic or inorganic acid in admixture with (b) a liquid or solid carrier, diluent or the like.

Both the anti-mycotic as well as the fungicidal composition may include other active constituents providing for complemental or synergistic effects.

Detailed Description of the Invention

According to a preferred method, the starting compound (III) for preparing the formula (I) target compound is a mercaptane or thiol, i.e. a compound in which Y stands for —SH, and this compound is reacted with a formula (II) starting compound in which X is a halogen atom, preferably chlorine, bromine or iodine, or an acid group capable of forming a reactive ester, e.g.

the toluene sulphonyl or methane sulphonyl radical or the like.

Suitable starting compounds of formula (II) are available or can be easily prepared by conventional methods from the corresponding carbinols which, in turn, may be obtained by reduction of ketones (cf. Godefroi, J. Med. Chem., Vol. 12, page 784, published 1969).

When reacting such estors or halides of formula (II), wherein $R^4$ is hydrogen, with mercaptanes or thiols of formula (III), precautions should be taken to prevent or minimize the competing reaction of splitting-off HX that would lead to formation of a styryl derivative of formula

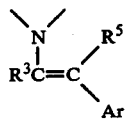

Suitable precautions include selection of suitable reaction conditions, i.e. solvent medium, reaction temperature and reaction time. As an example, a suitable reaction system involves use of an alkali metal carbonate in an aliphatic ketone at temperatures of below about 150° C.

Another suitable and preferred reaction system includes hexamethyl phosphoric triamide (also known as "Hexametapol") as the solvent or liquid medium with a reaction temperature of below about 75° C and reaction times of up to several days.

Alternatively, the formula (I) compounds can be obtained according to the invention by using a mercaptane or thiol as the formula (II) compound, i.e. X representing the group —SH, and reacting such formula (II) starting compound with a formula (III) starting compound in which Y is halogen of the type mentioned above or a reactive acid group, also as indicated above. Mercaptanes or thiols of formula (II) can be obtained by prior art methods, e.g. by reduction of a thioketone of the formula

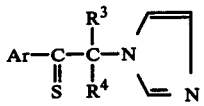

e.g. 1-thiophenacyl imidazole, with a metal hydride.

If the formula (I) compound is to be prepared and used in the form of an addition salt, the corresponding formula (I) compound can be reacted, in a manner known per se, with a suitable inorganic or organic acid, e.g. hydrochloric, nitric, sulphuric, phosphoric, acetic, adipic, butyric, oxalic, benzoic, salicylic, lactic, citric, cinnamic, phenylacetic, benzene dicarboxylic or fumaric acid.

Soluble addition salts of formula (I) compounds are preferred for many purposes. Addition salts formed with nitric acid represent a preferred group.

For preparing anti-mycotic pharmaceutical compositions containing at least one formula (I) compound or addition salt thereof, conventional methods, carriers, diluents or vehicles can be used, for example, as set forth in "Remington's Practice of Pharmacy" by E. W. Martin and E. F. Cook.

By the same token, fungicidal compositions for agricultural use can be obtained by conventional methods, such as described in Chapter 6 "Formulation" by E. Somers in Torgeson, "Fungicides", Vol. I, Academic Press, 1967.

The invention will be illustrated by means of the following non-limiting examples in which percentages are by weight.

EXAMPLE I

1-[β-(benzothiazolyl-2-thio)-2,4-dichlorophenethyl]-imidazole, nitrate salt

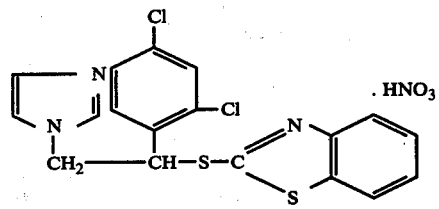

A three-necked flask provided with thermometer, reflux condenser and magnetic stirrer was used as a reactor and charged with a mixture of 15.03 g (90 millimoles, mM) 2-mercaptobenzothiazole, 9.0 g (65 mM) potassium carbonate (anhydrous, pulverized), 11.4 g (29mM) 1-(2,4-dichlorophenyl)-2-(1-imidazolyl)-ethyl chloride (in the form of the hydrochloride-semizinkchloride), 450 ml methyl isobutyl ketone and 0.75 g potassium iodide. The mixture was heated to reflux for 3 hours and the solution, while still hot, was filtered through a plied paper filter. The filtrated solution was evaporated under reduced pressure to yield 24.8 g of an oily residue that was dissolved in 500 ml of ethyl acetate and washed six times with 50 ml portions of 2 n aqueous sodium hydroxide. The aqueous extracts obtained were combined and re-extracted with 100 ml of ethyl acetate.

The organic phase of the extract was dried over $Na_2SO_4$, filtered and evaporated under reduced pressure. A brownish oil (14.1 g) was obtained as residue and dissolved in 50 ml of methanol. The solution obtained was treated with activated charcoal and filtered twice. The filtrate obtained was mixed with 7 ml of nitric acid (65% aqueous solution).

The target compound crystallized upon cooling of the acid mixture and 8.1 g of a beige colored crystalline solid having a melting point, m.p. of 187–188.5° C (decomposition) was obtained; yield = 17.3 mM or 60% of the theoretical yield. For analysis, the product was recrystallized from 150 ml of a 1:1 mixture (by volume) of ethanol and methanol to yield 6.0 g of colorless crystals, m.p. = 190–191° C (decomposition).

Analysis calculated for $C_{18}H_{13}Cl_2N_3S_2.HNO_3$ (mol. weight 469.4): C 46.05%, H 3.00%, N 11.94%, O 10.22%, S 13.66%. found: C 45.86%, H 2.84%, N 12.13%, O 10.11%, S 13.42%.

EXAMPLES II–XII

The following formula (I) compounds and addition salts were obtained by analogous methods, the melting point (m.p.) being indicated after each compound name:

1-[β-(2-benzoxazolylthio)-2,4-dichlorophenethyl]-imidazole, nitrate, m.p. 163–164.5° C 1-[β-(2-Δ²-thiazolinylthio)-2,4-dichlorophenethyl]-imidazole, nitrate, m.p. 137–139° C 1-[β-(5-chlorobenzothiazolyl-2-thio)-2,4-dichlorophenethyl]-imidazole, nitrate, m.p. 213–215° C 1-[β-(α-pyridylthio)-2,4-dichlorophenethyl]-imidazole, nitrate, m.p. 168–170° C 1-[β-(4,6-dimethylpyrimidyl-2-thio)-2,4-dichlorophenethyl]-imidazole, m.p. 140–141° C 1-[β-(1-methylimidazolyl-2-thio)-2,4-dichlorophenethyl]-imidazole, m.p. 117–119° C 1-[β-(quinolyl-2-thio)-2,4-dichlorophenethyl]-imidazole, m.p. 131–133° C 1-[β-(pyrimidyl-2-thio)-2,4-dichlorophenethyl]-imidazole, nitrate, m.p. 152–154° C 1-[β-(4-phenylthiazolyl-2-thio)-2,4-dichlorophenethyl]-imidazole, nitrate, m.p. 125–126° C 1-[β-(4-methylbenzothiazolyl-2-thio)-2,4-dichlorophenethyl]-imidazole, nitrate, m.p. 181–181.5° C 1-[β-(5-chloropyridyl-2-thio)-2,4-dichlorophenethyl]-imidazole, nitrate, m.p. 176–177° C The advantages of the present invention, as well as certain changes and modifications of the disclosed embodiments thereof, will be readily apparent to those skilled in the art. It is the applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

What is claimed is:

1. 1-[β-(2-benzoxazolylthio)-2,4-dichlorophenethyl]-imidazole and the acid addition salts thereof.

* * * * *